United States Patent
Adjei et al.

(10) Patent No.: US 7,074,388 B2
(45) Date of Patent: *Jul. 11, 2006

(54) WATER STABILIZED MEDICINAL AEROSOL FORMULATION

(75) Inventors: Akwete Adjei, Bridgewater, NJ (US); Anthony J. Cutie, Bridgewater, NJ (US)

(73) Assignee: KOS Life Science, Inc., Weston, FL (US)

( * ) Notice: Subject to any disclaimer, the term of this patent is extended or adjusted under 35 U.S.C. 154(b) by 19 days.

This patent is subject to a terminal disclaimer.

(21) Appl. No.: 10/234,825

(22) Filed: Sep. 3, 2002

(65) Prior Publication Data

US 2003/0091512 A1    May 15, 2003

Related U.S. Application Data

(63) Continuation-in-part of application No. 09/619,183, filed on Jul. 19, 2000, now abandoned, which is a continuation-in-part of application No. 09/209,228, filed on Dec. 10, 1998, now Pat. No. 6,261,539.

(51) Int. Cl.
*A61K 9/12* (2006.01)
*A61K 38/28* (2006.01)

(52) U.S. Cl. .......... 424/45; 424/434; 424/43; 424/489; 128/200.14; 514/866; 514/180

(58) Field of Classification Search ............ 424/45, 424/46, 43, 489, 434; 514/180, 866; 128/200.14
See application file for complete search history.

(56) References Cited

U.S. PATENT DOCUMENTS

| | | | |
|---|---|---|---|
| 5,695,744 A * | 12/1997 | Neale et al. ........... | 424/45 |
| 6,261,539 B1 * | 7/2001 | Adjei et al. ........... | 424/46 |
| 6,447,750 B1 * | 9/2002 | Cutie et al. ........... | 424/45 |
| 6,540,983 B1 * | 4/2003 | Adjei et al. ........... | 424/45 |
| 6,548,049 B1 * | 4/2003 | Cutie et al. ........... | 424/45 |
| 6,565,833 B1 * | 5/2003 | Cutie et al. ........... | 424/45 |

* cited by examiner

*Primary Examiner*—Sreeni Padmanabhan
*Assistant Examiner*—Mina Haghighatian
(74) *Attorney, Agent, or Firm*—Jonathan N. Provoost; Karen P. Bechtold

(57) ABSTRACT

This invention relates to a medicinal aerosol suspension formulation and more particularly, to a medicinal aerosol formulation containing a particulate drug or a combination of at least two particulate drugs, a propellant and a stabilizing agent comprising a water addition.

25 Claims, No Drawings

WATER STABILIZED MEDICINAL AEROSOL FORMULATION

RELATED APPLICATIONS

This application is a continuation-in-part of application U.S. Ser. No. 09/619,183, filed on Jul. 19, 2000, now abandoned which in turn is a continuation-in-part of application U.S. Ser. No. 09/209,228, filed Dec. 10, 1998, now U.S. Pat. No. 6,261,539 all of which are incorporated hereinto by reference in their entirety.

BACKGROUND OF THE INVENTION

1. Field of the Invention

This invention relates to a medicinal aerosol formulation, and more particularly, to a medicinal aerosol formulation comprising a stabilizer comprising a water addition.

2. Description of the Related Art

Delivery of drugs to the lung by way of inhalation is an important means of treating a variety of conditions, including such common local conditions as bronchial asthma and chronic obstructive pulmonary disease and some systemic conditions, including hormone replacement, pain management, cystic fibrosis, etc. Steroids, β2 agonists, anticholinergic agents, non-steroidal antiinflammatory agents, proteins and polypeptides are among the drugs that are administered to the lung for such purposes. Such drugs are commonly administered to the lung in the form of an aerosol of particles of respirable size (less than about 10 μm in diameter). The aerosol formulation can be presented as a liquid or a dry powder. In order to assure proper particle size in a liquid aerosol, as a suspension, particles can be prepared in respirable size and then incorporated into the suspension formulation containing a propellant. Alternatively, formulations can be prepared in solution form in order to avoid the concern for proper particle size in the formulation. Solution formulations must nevertheless be dispensed in a manner that produces particles or droplets of respirable size.

Once prepared an aerosol formulation is filled into an aerosol canister equipped with a metered dose valve. In the hands of the patient the formulation is dispensed via an actuator adapted to direct the dose from the valve to the patient.

It is important that an aerosol formulation be stable such that the pressurized dose discharged from the metered dose valve is reproducible. Rapid creaming, settling, or flocculation after agitation are common sources of dose irreproducibility in suspension formulations. This is especially true where a binary aerosol formulation containing only medicament and propellant, e.g. 1,1,1,2-tetrafluoroethane, is employed or where such formulation contains small amounts of surfactant as well. Sticking of the valve also can cause dose irreproducibility. In order to overcome these problems aerosol formulations often contain surfactants, which serve as suspending aids to stabilize the suspension for a time sufficient to allow for reproducible dosing. Certain surfactants also function as lubricants to lubricate the valve to assure smooth actuation. Myriad materials are known and disclosed for use as dispersing aids in aerosol formulations. Suitability of materials, however, is dependent on the particular drug and the propellant or class of propellant used in the formulation.

It is sometimes difficult to dissolve sufficient quantities of conventional surfactants in hydrofluorocarbon (HFC) propellants such as HFC-134a and HFC-227. Cosolvents, such as ethanol, have been used to overcome this problem, as described in U.S. Pat. No. 5,225,183. An alternative approach that avoids cosolvents involves materials that are soluble in hydrofluorocarbon propellants and are said to be effective surfactants or dispersing aids in an aerosol formulation. Among such materials are certain fluorinated surfactants and certain polyethyoxysurfactants.

It is known in the art that the presence of water in conventional aerosol formulations often result in a number of potential problems, e.g. stability of the formulation, erratic dose delivery, and, in some cases free radical reactions in the propellant. Therefore, it has generally been accepted that these preparations should be maintained substantially free of water. The rigorous exclusion of atmospheric moisture during both the manufacture and storage of such formulations, referred to as "developed" or "nascent" formulation water, increases the difficulties of preparing satisfactory stable aerosols containing the drug and raises the overall cost of the final product, especially when a moisture barrier, e.g. foil pouching, is included as a secondary package.

An exception had been found for beclomethasone dipropionate monohydrate. It has been reported that a formulation of this particular medicament combined with an amount of water in addition to its water of hydration is stable. In this regard, reference is made to U.S. Pat. No. 5,695,744 ("NEALE").

U.S. Pat. No. 5,695,744 (NEALE) relates to aerosol formulations for the administration of beclomethasone dipropionate monohydrate by inhalation, which comprises at least 0.015% by weight of water in addition to the water of crystallization associated with the monohydrate form of the medicament in order to preserve the solvate form of the drug as well its particle size properties. It is particularly claimed that the formulation must comprise at least 0.015% by weight of the formulation of water in addition to the water of crystallization associated with said monohydrate whereby said at least 0.015% water stabilizes the particle size of said beclomethasone dipropionate monohydrate particles. It is noted that other work by the NEALE in U.S. Pat. No. 5,833,950 [Aerosol formulations containing beclomethasone dipropionate-1, 1, 1, 2-tetrafluoroethane solvate] suggests that, for these beclomethasone dipropionate formulations to be stable in propellant fluids, notably—1,1,1,2-tetrafluoroethane, the medicament must be in fine crystalline solvate form, and preferably, that the formulations of the invention are substantially free of other potential solvating species such as chlorofluorocarbons, ethyl acetate, alkanes, ethers, alcohols and water. NEALE most importantly suggest that, in particular, the formulations of the solvate of the beclomethasone compound must be substantially free of water, for example containing less than 250 ppm, preferably less than 200 ppm, more preferably less than 100 ppm, for example less than 50 ppm water (U.S. Pat. No. 5,833,950, NEALE).

NEALE in these patents, discloses aerosol formulation technology for beclomethasone dipropionate monohydrate alone that substantially maintains intact the particular solvate form as well as its crystal shape, morphology, and other surface enegertic properties in the formulation. It is understood then that maintenance of the solvate form of the particulate medicament, together with its particle size properties, is the primary and only technically justifiable purpose of the NEALE patents.

What has not been appreciated, however, is that despite all efforts an amount of water develops in medicinal aerosol formulations during processing of such formulations which can not be eliminated and is always present ("developed" or "nascent" formulation water). Most surprising and unexpected is that such unstable formulations, containing nascent formulation water, can be and are stabilized by the presence of a concentration of water added in addition to the nascent or developed formulation water which stabilizes such medicament formulations.

SUMMARY OF THE INVENTION

It has surprisingly been found that novel medicinal aerosol formulations can be obtained without the use of either cosolvents, such as ethanol, or surfactants, such as sorbitan trioleate which are added to a binary aerosol formulation. Stable medicinal aerosol suspension formulations are obtained by the use of a water addition.

DETAILED DESCRIPTION OF THE INVENTION

This invention involves a stable suspension aerosol formulation suitable for pressurized delivery which comprises (1) a particulate medicament or drug or combination of at least two medicaments or drugs, (2) a suitable propellant, and (3) a stabilizer comprising a water addition.

A suitable medicament or drug is one which is suitable for administration by inhalation, the inhalation being used for oral and nasal inhalation therapy. Therapeutic categories of drugs or medicaments include cardiovascular drugs, antiallergics, analgesics, brochodilators, antihistamines, antitussives, antifungals, antivirals, antibiotics, pain medications, anti-inflammatories, peptides, proteins and steroids. Of course, not included within the medicaments of the subject invention are the solvates of a beclomethasone compound.

Particularly suitable medicaments or drugs include albuterol (also known as salbutamol), atropine, budesonide, cromolyn, epinephrine, ephedrine, fentanyl, flunisolide, formoterol, ipratropium bromide, isoproterenol, pirbuterol, prednisolone, mometasone, triamcinolone acetonide, salmeterol, amiloride, fluticasone, fluticasone esters, such as phosphate, monohydrate and furoate, (-)-4-amino-3,5-dichloro-α-[[[6(2-pyridinyl)ethoxy]hexyl]amino]methyl]benzenemethanol. Also included are the suitable acid addition salts of the foregoing drugs, their hydrates and their other solvates. In this regard, suitable acid addition salts include the salts obtained from inorganic acids, such as hydrochloric, hydrobromic, sulfuric, nitric, phosphoric and perchloric acids as well as organic acids such as tartaric, citric, acetic, succinic, maleic, fumaric and oxalic acids. Suitable pharmaceutically acceptable solvates include solvates with ethylactate, alkanes, ethers, alcohols and water.

A preferred embodiment of this invention are aerosol formulations which provide for a combination of at least two and most preferably not more than four different medicaments such as cardiovascular drugs, antiallergenics, analgesics, bronchodilators, antihistamines, antitussives, antifungal, antiviral, antibiotics, pain medications, anti-inflammatories, peptides, proteins and steroids and of the use of these aerosol formulations to treat the disease states associated with these medicaments. These medicaments and their use to treat a particular disease state are well known to a practitioner of the art.

Especially preferred, are formulation which comprise combinations comprising at least two different medicants, such as β2-adrenergic agonists, corticosteroids, anticholinergics and leucotriene modulators. Especially preferred are β2-adrenergic agonists, such as albuterol and formoterol and corticosteroids, such as mometasone, hydrocortisone, fludrocortisone, dexamethasone, prednisone, cortisone, aldosterone hemi-acetal, betamethasone, beclomethasone dipropionate, triamcinolone acetonide, budesonide dipropionate, fluticasone propionate and flunisolide, anticholinergics, such as ipratropium bromide, histamine antagonists (mast cell modulators), such as cromolyn and non-steroidal antiinflamatory agents, such as acetaminophen or ibuprofen.

This invention includes the derivatives of the foregoing medicaments. These derivatives include all the salt, ester, solvate and hydrate forms of the foregoing drugs as well as their geometric and optical isomers, including their chiral forms. Such derivatives are well known to a practitioner in this art.

The leucotrienes contemplated in this invention are those which are implicated as mediators of allergic and inflammatory responses associated with bronchial asthma and rheumatoid arthritis. This medicaments are known in the art to constrict dramatically the pulmonary airways and small blood vessels. Thus, inhibitors or antagonists of leucotrienes are effective mediators of the allergic responses typified by asthma and maybe used to treat bronchial asthma and other diseases states associated with inflammation of the airways.

The leucotriene modulators contemplated in this application include, but not limited to the following:

1. Inhibitors or antagonists of lecotriene, including the PAF receptor antagonists and 5-lipoxynase inhibitors, for example 2,5-diaryl tetrahydrofurans, 2,5-diaryl tetrahydrothiophenes, 2,4-diaryl tetrahydrofurans, 2,4-diaryl tetrahydrothiophenes, 1,3-diaryl cyclopentanes, 2,4-diaryl pyrrolidines, and 2,5-diaryl pyrrolidines, triazolo(4,3-A)(1,4)benzodiazepines and thieno (3,2F)(1,2,4)triazolo(4,3-A)(1,4)diazepine compounds, 6-phenyl-4H-s-triazolo[4,3-a][1,4]benzodiazepines (see, U.S. Pat. Nos. 5,856,323; 5,358,938; 4,959,361; and 3,987,052), including, both optically pure and racemates (U.S. Pat. No. 5,629,337). An example of this group of compounds is Zileuton® (Abbott Laboratories) and Acolate® (Merck).

2. Chromone-2-carboxylic acid derivatives as antagonists of SRS-A (slow reacting substance of anaphylaxis (see, Samuelsson et al., Department of Chemistry, Karolinska Institutet, Stockholm, Sweden, TIPS, 227, May, 1980; J. Med. Chem. 20 371 (1977)), such as 7-[3-(4-acetyl-3-hydroxy-2-propylphenoxy)-2-hydroxypropoxy]-4-oxo-8-propyl-4H-1-benzopyran-2-carboxylate (FPL 55712), which is a specific antagonist of SRS-A as well as a standard for evaluating other inhibitors;

3. Aryloxyalkyloxy-and aralkyloxy-4-hydroxy-3-nitrocoumarins as antagonists of SRS-A and inhibitors of histamine release, (see. e.g. Buckle et al., J. Med. Chem. 22 158 (1979); U.S. Pat. No. 4,296,237; European Patent No. 0036663; U.S. Pat. No. 4,296,120; and U.S. Pat. No. 4,296,129), as well as other compounds which act as inhibitors of SRS-A including oxiranbutyric acid esters, 3-hydroxy-4-substituted-3-pyrroline-2,5-diones or carboxy-oxo-pyrrolidino)phenyl alkenamides and esters or (carboxyacylamino)phenyl alkenamides and esters, or the substituted derivatives of these before mentioned compounds, including, but not limited, to alkyl, hydroxy amino, dialkylamino, hydroxymethyl, aminomethyl, alkylaminomethyl or alkanoylaminomethyl of 1 to 12 carbon atoms; —CN, —CONH$_2$ or —CO$_2$M in which M is hydrogen, aryl, phenyl, or naphthyl, cyclohexyl, cyclopentyl, or fluoromethoxy; or 4. Antagonists and inhibitors of leukotriene including N-o-tolylsulfonylbenzamide compounds.

All of the aforementional prior literature is expressly incorporated by reference. These medicaments are known in the art to treat inflammatory diseases and include medicaments that block the release, production, secretion, or any other biochemical action arachidonic acid, prostaglandins and thromboxanes, or other leukotrienes that participate in inflammatory reactions, exhibit chemotactic activities, stimulate lysosomal enzyme release and act as important factors in the immediate hypersensitivity reaction.

Especially preferred medicaments include groups comprising [1-formyl-5-(cyclopentyloxycarbonyl)amino-1H-indol-3-ylmethyl]-3-methoxy-N-o-tolylsulfonylbenzamide, [1-(hydroxycarbamoyl)-5-(cyclopentyloxycarbonyl)amino-1H-indol-3-ylmethyl]-3-methoxy-N-o-tolylsulfonylbenzamide, [1-((2-carboxyethyl)carbamoyl)-5-(cyclopentyloxycarbonyl)amino-1H-indol-3-ylmethyl]-3-methoxy-N-o-tolylsulfonylbenzamide, [1-((2-tetrazolylethyl)carbamoyl)-5-(cyclopentyloxycarbonyl)amino-1H-indol-3-ylmethyl]-3-methoxy-N-o-tolylsulfonylbenzamide, [1-(methylphenylcarbamoyl)-5-(cyclopentyloxycarbonyl)amino-1H-indol-3-ylmethyl]-3-methoxy-N-o-tolylsulfonylbenzamide, [1-(diphenylcarbamoyl)-5(cyclopentyloxycarbonyl)amino-1H-indol-3-ylmethyl]-3-methoxy-N-o-tolylsulfonylbenzamide; [1-carbamoyl-5-(cyclopentyloxycarbonyl)amino-1H-indol-3-ylmethyl]-3-methoxy-N-o-tolylsulfonylbenzamide, and [1-(pyrrolidinecarbonyl)-5-(cyclopentyloxycarbonyl)amino-1H-indol-3-ylmethyl]-3-methoxy-N-o-tolylsulfonylbenzamide. Also, pharmaceutically acceptable salts of these agents, including addition salts derived from organic or inorganic acids such as hydrochloric, hydrobromic, sulfuric, phosphoric, methane sulfonic, nitric, p-toluene sulfonic, acetic, citric, maleic, succinic acid and the like. In addition, the compounds in their free carboxylic acid form may be converted by standard techniques well-known to the practioner to their corresponding alkali metal (e.g. sodium or potassium), alkaline earth metal (e.g. calcium or magnesium), ammonium or primary, secondary and tertiary alkylamine salts, the latter containing from 1 to 6 carbon atoms in their alkyl moieties or a pharmaceutically acceptable salt thereof. These components are known in the literature and are described, for example in Brown et al., J. Med. Chem., vol. 35(13), pp. 2419 to 2439 (1992) Jacobs et al., J. Med. Chem., vol. 37(9), pp. 1282 to 1297 (1994); AU 646 587 Australia March 1993; McFadden, E. R., Jr., Am Rev. Resp. Dis., vol. 147 pp. 1306–1310 (1993); Greenberger, P. A., Chest, vol. 101 pp. 418S–421S (1992); Lipworth, B. J. Pharmacol. Ther., vol. 58 pp. 173–209 (1993); Busse, W. W., Chest, vol. 104 pp. 1565–1571 (1993); Anonymous, Executive Summary: Guidelines for the Diagnosis and Management of Asthma, Public Health Service, Publication 91-3042A, NIH, Bethesda, Md., pp. 1–44 (1991); Israel, E., and Drazen, J. M., N. Engl. J. Med., vol., 331 pp. 737–739 (1994); or Barnes, P. J., N. Engl. Med., vol. 332 pp. 868–875 (1995). All these prior publications are expressly incorporated by reference.

For purposes of the formulations of this invention, which are intended for inhalation into the lungs, the medicament or drug is preferably micronized whereby a therapeutically effective amount or fraction (e.g., ninety percent or more) of the drug is particulate. Typically, the particles have a diameter of less than about 10 microns, and preferably less than about 5 microns, in order that the particles can be inhaled into the respiratory tract and/or lungs.

The particulate medicament or drug is present in the inventive formulations in a therapeutically effective amount, that is, an amount such that the drug can be administered as an aerosol, such as topically, or via oral or nasal inhalation, and cause its desired therapeutic effect, typically preferred with one dose, or through several doses. The particulate drug is administered as an aerosol from a conventional valve, e.g., a metered dose valve.

The term "amount" as used herein refers to quantity or to concentration as appropriate to the context. The amount of a drug that constitutes a therapeutically effective amount varies according to factors such as the potency of the particular drug, the route of administration of the formulation, and the mechanical system used to administer the formulation. A therapeutically effective amount of a particular drug can be selected by those of ordinary skill in the art with due consideration of such factors. Generally a therapeutically effective amount will be from about 0.001 parts by weight to about 2 parts by weight based on 100 parts by weight of the propellant.

A suitable propellant is selected. A suitable propellant is any fluorocarbon, e.g. a 1–4 hydrogen containing flurocarbon(, such as $CHF_2CHF_2$, $CF_3CH_2F$, $CH_2F_2CH_3$ and $CF_3CHFCF_3$)), a perfluorocarbon, e.g. a 1–4 carbon perfluorocarbon, (such as $CF_3CF_3$, $CF_3CF_2CF_3$); or any mixture of the foregoing, having a sufficient vapor pressure to render them effective as propellants. Some typical suitable propellants include conventional chlorofluorocarbon (CFC) propellants such as mixtures of propellants 11, 12 and 114. Non-CFC propellants such as 1,1,1,2-tetrafluoroethane (Propellant 134a), 1,1,1,2,3,3,3-heptafluoropropane (Propellant 227) or mixtures thereof are preferred. The propellant is preferably present in an amount sufficient to propel a plurality of the selected doses of drug from an aerosol canister.

A suitable stabilizer is selected. A suitable stabilizer is a "water addition". As used herein a "water addition" is an amount of water which (1) is added, either initially with other components of the aerosol formulation, e.g. medicament and propellant, or after the other components, e.g. medicament, propellant, are combined and processed, (2) is in addition to the water which is always present and which develops during processing and/or storage of the aerosol formulation, i.e. "developed" or "nascent" formulation water, and (3) is present in an amount which stabilizes the ordinarily unstable medicinal aerosol dispersion formulation having nascent formulation water.

An aerosol formulation preferably comprises the water addition in an amount effective to stabilize the formulation relative to an identical formulation not containing the water addition, i.e. containing only nascent formulation water, such that the drug does not settle, cream or flocculate after agitation so quickly as to prevent reproducible dosing of the drug. Reproducible dosing can be achieved if the formulation retains a substantially uniform drug concentration for about two or three seconds after agitation.

The particular amount of the water addition that constitutes an effective amount is dependent upon the particular propellant and on the particular drug used in the formulation. It is therefore not practical to enumerate specific effective amounts for use with specific formulations of the invention, but such amounts can readily be determined by those skilled in the art with due consideration of the factors set forth above. Generally, however, the water addition must be present in a formulation in an amount in excess of the concentration of the nascent formulation water. Such concentration of nascent formulation water typically ranges up to 300 parts by weight per one million parts by weight of the total weight of the aerosol formulation. Accordingly, the water addition in excess of this nascent water concentration typically ranges from about 300 parts by weight to 2000 parts by weight per one million parts by weight of the total aerosol formulation weight. Preferred is an amount ranging from about 500 parts by weight to about 2000 parts weight based on 1 million parts by total weight of the formulation. Most preferred is that the concentration of the water addition is from 500 parts by weight to 700 parts by weight per one million parts by weight of the total weight of the medicinal aerosol formulation.

It is to be emphasized that this is an amount which exceeds the amount of nascent or developed formulation water. It is also to be stressed that this amount of water addition can be added and initially combined with the other components of the formulation, e.g. medicament, such as triamcinolone acetonide, and propellant, e.g. 1,1,1,2-tetrahydrofluoroethane, or added to the resultant formulation after these other components have been processed, e.g. prior to or subsequent to storage.

It has surprisingly been found that the formulation of the invention is stable without the necessity of employing a cosolvent, such as ethanol, or surfactants. However, further components, such as conventional lubricants or surfactants, cosolvents, ethanol, etc., can also be present in an aerosol formulation of the invention in suitable amounts readily determined by those skilled in the art. In this regard, reference is made to U.S. Pat. No. 5,225,183, which is incorporated by reference hereinto in its entirety.

A most preferred formulation comprises the medicament, the propellant, the ethanol cosolvent and the water addition, for example, triamcinolone acetonide, budesonide, fluticasone, or mometasone, 1,1,1,2-tetrafluoroethane, ethanol and the water addition.

Generally the formulations of the invention can be prepared by combining (i) the drug in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular stabilizer and other adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations of the invention are preferably dispensed via a valve assembly wherein the diaphragm is made of a nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMER™ GERS 1085 NT polyolefin (Union Carbide).

Conventional aerosol canisters, coated or uncoated, anodized or unanodized, e.g., those of aluminum, glass, stainless steel, polyethylene terephthalate, and coated canisters or cans with epon, epoxy, etc., can be used to contain a formulation of the invention.

The formulation of the invention can be delivered to the respiratory tract and/or lung by oral inhalation in order to effect bronchodilation or in order to treat a condition susceptible of treatment by inhalation, e.g., asthma, chronic obstructive pulmonary disease. The formulations of the invention can also be delivered by nasal inhalation in order to treat, e.g., allergic rhinitis, rhinitis, (local) or diabetes (systemic), or they can be delivered via topical (e.g., buccal) administration in order to treat, e.g., angina or local infection.

What is claimed is:

1. A medicinal aerosol formulation comprising:

(a) a therapeutically effective amount of at least one particulate medicament which does not include a solvate of a beclomethasone compound;

(b) a propellant; and (c) a stabilizer consisting of water, in addition to nascent water present in the formulation, in an amount ranging from about 300 parts by weight to about 2000 parts by weight to one million parts by total weight of the formulation.

2. The medicinal aerosol formulation of claim 1, wherein the at least one particulate medicament is selected from the group consisting of β-2 adrenergic agonists, corticosteroids, anti-cholinergics, histamine antagonists, non-steroidal anti-inflammatory agents and leucotriene modulators.

3. The medicinal aerosol formulation of claim 2, wherein the β-2 adrenergic agonists are selected from the group consisting of albuterol, formoterol and pharmaceutically acceptable salts, esters, optical isomers and geometric isomers thereof.

4. The medicinal aerosol formulation of claim 2, wherein the corticosteroid is selected from the group consisting of monetasone, hydrocortisone, fludrocortisone, dexamethasone, prednisone, cortisone, aldosterone hemi-acetal, betametasone, triamcinolone acetonide, budesonide, dipropionate, fluticasone, flunisolide and pharmaceutically acceptable salts, esters, hydrates, solvates, optical isomers and geometric isomers thereof.

5. The medicinal aerosol formulation of claim 4, wherein the corticosteroid is fluticasone or fluticasone propionate.

6. The medicinal aerosol formulation of claim 2, wherein the corticosteroid is a non-solvated form of beclomethasone dipropionate.

7. The medicinal aerosol formulation of claim 2, wherein the anti-cholinergic is cromolyn or a pharmaceutically acceptable salt or ester thereof.

8. The medicinal aerosol formulation of claim 2, wherein the leucotriene modulator is selected from the group consisting of [[1-formyl-5-(cyclopentyloxycarbonyl)amino-1H-indol-3-ylmethyl]-3-methoxy-1-N-o-tolylsulfonylbenzamide, [1-(hydroxycarbamoyl)-5-(cyclopentyloxycarbonyl) amino-1H-indol-3-ylmethyl]-3-methoxy-N-o-tolylsulfonylbenzamide, [1-((2-carboxyethyl)carbamoyl)-5-(cyclopentyloxycarbonyl)amino-1H-indol-3-ylmethyl]-3-methoxy-N-o-tolylsulfonylbenzamide, [1-((2-tetrazolylethyl)carbamoyl)-5-(cyclopentyloxycarbonyl) amino-1H-indol-3-ylmethyl]-3-methoxy-N-o-tolylsulfonylbenzamide, [1-(methylphenylcarbamoyl)-5-

(cyclopentyloxycarbonyl)amino-1H-indol-3-ylmethyl]-3-methoxy-N-o-tolylsulfonylbenzamide; [1-(diphenylcarbamoyl)-5-(cyclopentyloxycarbonyl)amino-1H-indol-3-ylmethyl]-3 -methoxy-N-o-tolylsulfonylbenzamide; [1-carbamoyl-5-(cyclopentyloxycarbonyl)amino-1H-indol-3-ylmethyl]-3-methoxy-N-o-tolylsulfonylbenzamide, [1-(pyrrolidine-carbonyl)-5-(cyclopentyloxycarbonyl)amino-1H-indol-3-ylmethyl]-3-methoxy-N-o-tolylsulfonylbenzamide, and pharmaceutically acceptable salts thereof.

9. The medicinal aerosol formulation of claim 1, wherein the at least one particulate medicament is selected from the group consisting of albuterol, atropine, budesonide, cromolyn, epinephrine, ephedrine, fentanyl, flunisolide, formoterol, ipratropium bromide, isoproterenol, pirbuterol, prednisone, triamcinolone acetonide, salmeterol, amiloride, fluticasone, (−)4-amino-3,5-dichloro-α-[[[6(2-pyridinyl)ethoxy]hexyl]amino]methyl]benzene-methanol and pharmaceutically acceptable esters, hydrates and solvates thereof.

10. The medicinal aerosol formulation of claim 9, wherein the at least one particulate medicament is budesonide, formoterol or fluticasone.

11. The medicinal aerosol formulation of claim 10, wherein the at least one particulate medicament is fluticasone.

12. The medicinal aerosol formulation of claim 9, wherein the at least one particulate medicament is triamcinolone acetonide.

13. The medicinal aerosol formulation of claim 1, wherein the at least one particulate medicament is a combination selected from the group consisting of (a) a corticosteroid and a β-2 adrenergic agonist, (b) a corticosteroid and an anticholinergic agent, (c) a corticosteroid and a leucotriene modulator, (d) a corticosteroid, a β-2 adrenergic agonist and a leucotriene modulator, (e) a β-2 adrenergic agonist and a leucotreine modulator, (f) a β-2 adrenergic agonist and an anticholinergic agent, (g) a non-steroidal anti-inflammatory agent and a histamine antagonist, and (h) fluticasone and an anticholinergic agent.

14. The medicinal aerosol formulation of claim 1, wherein said propellant is selected from the group consisting of 1,1,1,2-tetrafluoroethane, 1,1,1,2,3,3,3-heptafluoropropane and a mixture thereof.

15. The medicinal aerosol formulation of claim 1, wherein said stabilizer is present in an amount ranging from about 500 parts by weight to about 2000 parts weight based on one million parts by total weight of the formulation.

16. The medicinal aerosol formulation of claim 15, wherein said stabilizer is present in an amount ranging from about 500 parts by weight to about 700 parts by weight to one million parts by total weight of the formulation.

17. The medicinal aerosol formulation of claim 1 further comprising a cosolvent.

18. The medicinal aerosol formulation of claim 17 wherein the cosolvent is ethanol.

19. The medicinal aerosol formulation of claim 1, wherein the formulation is in an aerosol canister equipped with a metered dose valve.

20. A metered dose inhaler containing the medicinal aerosol formulation of claim 1.

21. A method of making a medicinal aerosol formulation comprising (a) a therapeutically effective amount of at least one particulate medicament which does not include a solvate of a beclomethasone compound; (b) a propellant; and (c) a stabilizer consisting of water, in addition to nascent water present in the formulation, in an amount ranging from about 300 parts by weight to about 2000 parts by weight to one million parts by total weight of the formulation, said method comprising the steps of:
 (1) either (i) combining said at least one particulate medicament, propellant and water or (ii) combining said at least one particulate medicament and propellant, followed by the addition of water; and
 (2) dispersing said at least one particulate medicament, propellant and water.

22. A medicinal aerosol formulation made according to the method of claim 21.

23. The method of claim 21, wherein the medicinal aerosol formulation further comprises a cosolvent, wherein step (1) comprises either (I) combining said at least one particulate medicament, propellant, cosolvent and water or (ii) combining said at least one particulate medicament, propellant and cosolvent, followed by the addition of water, and wherein step (2) comprises dispersing said at least one particulate medicament, propellant, cosolvent and water.

24. A medicinal aerosol formulation made according to the method of claim 23.

25. A method of stabilizing a medicinal aerosol formulation comprising (a) a therapeutically effective amount of at least one particulate medicament which does not include a solvate of a beclomethasone compound and (b) a propellant, said method comprising the step of:
 adding a stabilizer consisting of water, in addition to nascent water present in the formulation, in an amount ranging from about 300 parts by weight to about 2000 parts by weight to one million parts by total weight of the formulation,
 whereby the at least one particulate medicament does not settle, cream or flocculate so quickly after agitation as to prevent reproducible dosing thereof.

* * * * *